United States Patent
Munro et al.

(10) Patent No.: US 10,688,215 B2
(45) Date of Patent: Jun. 23, 2020

(54) FLEXIBLE HYDROGEL WOUND DRESSINGS

(71) Applicant: FIRST WATER LIMITED, Wiltshire (GB)

(72) Inventors: Hugh Semple Munro, Warwickshire (GB); Philip Andrews, Wiltshire (GB)

(73) Assignee: FIRST WATER LIMITED, Wiltshire (GB)

( * ) Notice: Subject to any disclaimer, the term of this patent is extended or adjusted under 35 U.S.C. 154(b) by 758 days.

(21) Appl. No.: 15/031,333

(22) PCT Filed: Oct. 24, 2014

(86) PCT No.: PCT/GB2014/053189
§ 371 (c)(1),
(2) Date: Apr. 22, 2016

(87) PCT Pub. No.: WO2015/059501
PCT Pub. Date: Apr. 30, 2015

(65) Prior Publication Data
US 2016/0250373 A1    Sep. 1, 2016

(30) Foreign Application Priority Data
Oct. 24, 2013  (GB) .................................. 1318842.0

(51) Int. Cl.
*A61L 15/42*    (2006.01)
*A61L 15/60*    (2006.01)
(Continued)

(52) U.S. Cl.
CPC .......... *A61L 15/42* (2013.01); *A61F 13/0206* (2013.01); *A61F 13/0263* (2013.01);
(Continued)

(58) Field of Classification Search
CPC ........ A61L 15/42; A61L 15/425; A61L 15/24; A61L 15/26; A61L 15/58; A61L 15/60;
(Continued)

(56) References Cited

U.S. PATENT DOCUMENTS 3,457,919 A  *  7/1969  Harbard ................ A61F 13/023
                                                    602/55
5,112,618 A  *  5/1992  Cartmell ............. A61F 13/0203
                                                    424/443
(Continued)

FOREIGN PATENT DOCUMENTS

EP          1658865 A1    5/2006
EP          2572737 A1    3/2013
(Continued)

OTHER PUBLICATIONS

Clarke, "The Impact of Iodozyme and Oxyzyme on Wound Healing and Quality of Life", Stafforshire and Stoke on Trent Partnership, Poster Presentation at The 2013 Wounds UK Conference, Harrogate, England, UK (Nov. 2013).

*Primary Examiner* — Tarla R Patel
(74) *Attorney, Agent, or Firm* — Nixon Peabody LLP; Ronald I. Eisenstein; Nicole D. Kling (57) ABSTRACT

Disclosed herein is a wound dressing and composition comprising a backing layer having disposed thereon a discontinuous layer of hydrogel, wherein the discontinuous layer of hydrogel is in the form of discrete islands of hydrogel on the backing layer. Methods of treating a wound using the dressing or the composition are also disclosed. Methods of forming the dressing or the composition are also disclosed.

18 Claims, 4 Drawing Sheets

(51) Int. Cl.
*A61F 13/02* (2006.01)
*A61L 15/24* (2006.01)
*A61L 15/26* (2006.01)
*A61L 15/58* (2006.01)
*B05D 3/06* (2006.01)

(52) U.S. Cl.
CPC .............. *A61L 15/24* (2013.01); *A61L 15/26* (2013.01); *A61L 15/425* (2013.01); *A61L 15/58* (2013.01); *A61L 15/60* (2013.01); *A61L 2420/02* (2013.01); *B05D 3/067* (2013.01); *B05D 2201/02* (2013.01); *B05D 2401/20* (2013.01); *B05D 2502/005* (2013.01)

(58) Field of Classification Search
CPC ............ A61L 2420/02; A61F 13/0263; A61F 13/0206; B05D 3/067; B05D 2201/02; B05D 2401/20; B05D 2502/005
USPC .......................................................... 602/55
See application file for complete search history.

(56) References Cited

U.S. PATENT DOCUMENTS

| | | | | |
|---|---|---|---|---|
| 5,308,313 A * | 5/1994 | Karami | ................ | A61F 13/025 602/54 |
| 6,689,931 B2 * | 2/2004 | Etheredge, III | .... | A61F 13/0206 602/41 |
| 6,953,602 B2 * | 10/2005 | Carte | .................... | A61F 13/023 427/208.4 |
| 7,223,899 B2 * | 5/2007 | Sigurjonsson | ...... | A61F 13/0203 602/41 |
| 10,086,107 B2 * | 10/2018 | Cotton | .................... | A61L 15/42 |
| 2004/0126413 A1 | 7/2004 | Fertram et al. | | |
| 2006/0251880 A1 * | 11/2006 | Munro | ................. | A61L 15/425 428/304.4 |
| 2010/0266794 A1 * | 10/2010 | Wright | .................... | A61L 15/60 428/35.7 |
| 2012/0123220 A1 * | 5/2012 | Iyer | ........................ | A61L 15/42 600/300 |
| 2014/0171851 A1 * | 6/2014 | Addison | ............... | A61F 13/025 602/55 |

FOREIGN PATENT DOCUMENTS

| | | |
|---|---|---|
| WO | 1993/04691 A1 | 3/1993 |
| WO | 1993/10795 A1 | 6/1993 |
| WO | 1996/02270 A1 | 2/1996 |
| WO | 1997/24149 A1 | 7/1997 |
| WO | 1997/34947 A1 | 9/1997 |
| WO | 2000/06214 A1 | 2/2000 |
| WO | 2000/06215 A1 | 2/2000 |
| WO | 2000/07638 A1 | 2/2000 |
| WO | 2000/46319 A1 | 8/2000 |
| WO | 2000/65143 A1 | 11/2000 |
| WO | 2001/96422 A1 | 12/2001 |
| WO | 2009/098518 A2 | 8/2009 |

* cited by examiner

FLEXIBLE HYDROGEL WOUND DRESSINGS

CROSS-REFERENCE TO RELATED APPLICATIONS

This application is a 35 U.S.C. § 371 National Phase Entry Application of International Application No. PCT/GB2014/053189 filed Oct. 24, 2014, which designated the U.S., and which claims benefit of GB Application No. 1318842.0 filed Oct. 24, 2013, the contents of each of which are incorporated herein by reference in their entireties.

FIELD OF THE INVENTION

The present invention relates to wound dressings comprising hydrogels and their manufacture, and, in some embodiments, to composites, comprising cross-linked hydrogels and water-absorbent foam and/or aqueous solution swellable fibrous materials, having improved flexibility.

The expression "hydrogel" and like expressions, used herein, are not to be considered as limited to gels which contain water, but extend generally to all hydrophilic gels and gel compositions, including those containing organic non-polymeric components in the absence of water.

BACKGROUND OF THE INVENTION

Hydrogels are macromolecular networks swollen partially or to equilibrium with a suitable fluid, normally an aqueous fluid. Hydrogels can swell in water but do not dissolve. It is known that hydrogels are useful in a number of biomedical applications, including but not limited to wound and burns dressings, biomedical electrodes and skin adhesives, particularly because of their ability to donate and absorb fluid and hence maintain a moist but not wet environment.

There are, however, disadvantages with prior art wound dressings comprising hydrogel compositions in that the flexibility of the dressings can be poor. This is particularly evident when the hydrogel comprises a scrim material used to provide mechanical strength to the hydrogel. Typical scrim materials used comprise non-woven fibres. The scrim material can be within the hydrogel and or present as a support layer on which the hydrogel is formed.

Poor flexibility of the hydrogel can lead to difficulties in applying wound dressings to various parts of the body.

There is a need to provide wound dressings comprising hydrogels with improved flexibility, while still being able to provide the fluid handling and wound treatment properties of the prior art hydrogels.

BRIEF DESCRIPTION OF THE INVENTION

The present invention relates to a wound dressing comprising a hydrogel possessing improved flexibility. Herein is also provided a method of forming the wound dressing. The wound dressings comprising a hydrogel may be produced by a method comprising: forming discrete shaped islands of hydrogel and arranging them into an array disposed on a backing layer. The discrete and discontinuous nature of the hydrogel regions provides greater flexibility to a wound dressing comprising such a structure. Preferable and optional features will be described herein. Any preferable or optional feature may be combined with any aspect or embodiment of the invention or any other preferable or optional feature.

In an embodiment, there is provided a wound dressing comprising a backing layer having disposed thereon a discontinuous layer of hydrogel, wherein the discontinuous layer of hydrogel is in the form of discrete islands of hydrogel on the backing layer. The backing layer is preferably a non-hydrogel-containing layer. The backing layer acts to support the discrete islands of hydrogel, so that they can remain in an array when, for example, placed on a wound. The backing layer is preferably a flexible material, such that it can conform around the contours of a human body. The backing layer has disposed thereon a discontinuous layer of hydrogel, but the hydrogel need not necessarily contact the backing layer, and one or more further layers, e.g. the support layer, may be disposed between the backing layer and the discontinuous layer of hydrogel. Each island may comprise, consist essentially of or consist of hydrogel. "Consist essentially of" indicates that the island comprises at least 80 wt % hydrogel, optionally at least 90 wt % hydrogel, optionally at least 95 wt % hydrogel, optionally at least 98 wt % hydrogel, including any water that may be present in the hydrogel. The wound may be an acute or a chronic wound.

In an embodiment, there is provided a composition comprising a discontinuous layer of hydrogel, wherein the composition is for use in the treatment of a wound, the composition further comprising a backing layer having disposed thereon the discontinuous layer of hydrogel, wherein the discontinuous layer of hydrogel is in the form of discrete islands of hydrogel on the backing layer. The backing layer is preferably a non-hydrogel-containing layer. The backing layer acts to support the discrete islands of hydrogel, so that they can remain in an array when, for example, placed on the wound.

In an embodiment, there is provided a method of treating a wound, the method comprising applying a wound dressing described herein or a composition described herein to the wound, and wherein the hydrogel is disposed between the backing layer and the wound, and, optionally the hydrogel contacts the wound. As described herein, an absorbent layer may be disposed on a side of the islands of hydrogel facing away from the backing layer, and, in the method of treating the wound, the absorbent layer may contact the wound.

"Discrete islands of hydrogel" can indicate that the islands of hydrogel do not touch one another, i.e. are not linked by hydrogel. The islands are typically disposed on and project above a surface of the backing layer, and the backing layer is not a hydrogel; the backing layer may be or comprises a polymeric film, e.g. a breathable polymeric film, as described herein. As described herein, a supporting layer may be disposed between at least some of the discrete islands of hydrogel and the backing layer.

The islands, when viewed from an angle perpendicular to the plane backing layer, may each have shape selected from a regular or irregular shape, or a combination thereof. The islands may each have a shape selected from polygons, dots and crosses or combinations thereof.

Optionally, the closest distance between two adjacent islands of hydrogel is at least 50 microns, optionally at least 500 microns. Optionally, the closest distance between two adjacent islands of hydrogel is 10 mm or less, optionally 5 mm or less. Optionally, the closest distance between two adjacent islands of hydrogel is from 50 microns to 5000 microns, optionally from 100 microns to 5000 microns, optionally from 500 to 5000 microns, optionally from 1 mm to 5 mm, optionally from 2 to 4 mm, optionally from 2.5 mm to 3.5 mm, optionally about 3 mm.

Optionally, at least some, optionally all of the discrete islands on the backing layer, each have an area, extending across the backing layer, of at least 1 mm$^2$ optionally at least 5 mm$^2$. Optionally, at least some, optionally all of the discrete islands on the backing layer, each have an area, extending across the backing layer, of from 5 mm$^2$ to 500 mm$^2$, optionally from 25 mm$^2$ to 250 mm$^2$, optionally from 50 mm$^2$ to 100 mm$^2$.

Optionally, the closest distance between two adjacent islands of hydrogel is from 50 microns to 5000 microns, optionally from 100 microns to 5000 microns, optionally from 500 microns to 5000 microns, optionally from 1 mm to 5 mm, optionally from 2 to 4 mm, optionally from 2.5 mm to 3.5 mm, optionally about 3 mm, and at least some, optionally all of the discrete islands on the backing layer, each have an area, extending across the backing layer, of from 5 mm$^2$ to 500 mm$^2$, optionally from 25 mm$^2$ to 250 mm$^2$, optionally from 50 mm$^2$ to 100 mm$^2$. Optionally, the closest distance between two adjacent islands of hydrogel is from 1 mm to 5 mm, and at least some, optionally all of the discrete islands on the backing layer, each have an area, extending across the backing layer, of from 50 mm$^2$ to 100 mm$^2$.

In use, the discontinuous layer of hydrogel may be disposed on a wound-facing side of the backing layer. In use, the hydrogel may be able to contact a wound.

Optionally, the backing layer comprises a polymeric film. The polymeric film may comprise or be a polyurethane film. Optionally, the polymeric film, which may be or comprise a polyurethane film, is breathable. The polymeric film may have an MVTR of at least 10 g/m$^2$/24 hours, optionally at least at least 50 g/m$^2$/24 hours, optionally at least 100 g/m$^2$/24 hours, optionally at least 200 gm$^2$/24 hours, optionally at least 300 g/m$^2$/24 hours, optionally at least 500 g/m$^2$/24 hours, optionally at least 1000 g/m$^2$/24 hours, with MVTR as measured by the method described in 1993 BP Appendix XX J1. The polymeric film may have an MVTR of from 100 g/m$^2$/24 hours to 10000 g/m$^2$/24 hours, optionally an MVTR of from 100 g/m$^2$/24 hours to 1000 g/m$^2$/24 hours with MVTR as measured by the method described in 1993 BP Appendix XX J1.

In use, an adhesive layer may be disposed on at least a part of a wound-facing side of the backing layer, and the adhesive can act to adhere the discrete islands of hydrogel, and, if present any supporting layer on the discrete islands, to the backing layer and/or can adhere the wound dressing to the skin of a user of the dressing.

Optionally, an adhesive is disposed between the backing layer and at least some, optionally all, of the discrete islands of hydrogel. The adhesive may be any suitable adhesive, which may be or comprise an acrylic adhesive and/or a pressure sensitive adhesive, optionally a pressure sensitive, acrylic adhesive.

Optionally, at least some, optionally all, of the discrete islands of hydrogel have disposed thereon or therein a supporting layer. Optionally, the discrete islands of hydrogel comprise a supporting layer on a non-wound facing side wherein the supporting layer adheres at least in part to the backing layer and or adhesive layer. The supporting layer be or comprise a scrim. The scrim may be a woven or non-woven fabric, or a net, and optionally is non-water absorbent. The scrim material may be integral with—i.e. suitably embedded within—the discrete islands of hydrogel. Such a scrim material may be formed of a material that is natural in origin, synthetic in origin, or partly natural and partly synthetic. The scrim may suitably be in the form of a net or a woven or non-woven fabric. Preferred scrims include those formed from polyolefins, polyamides, polyacrylates, or polyesters, for example non-wovens, foams or nets.

If a supporting layer is embedded within the discrete islands of hydrogel, the supporting layer, e.g. scrim material, may be disposed closer to one side of the hydrogel than the other, e.g. closer to the side of the hydrogel facing away from the backing layer than the side of the hydrogel facing away from the wound, or closer to the side of the hydrogel facing away from the wound than the side of the hydrogel facing away from the backing layer. In an embodiment, the supporting layer, e.g. scrim material, may be embedded within the hydrogel, such that the hydrogel forms a relatively thin layer over the supporting layer, and this relatively thin layer of hydrogel can contact the adjacent layer (e.g. the backing layer, the absorbent layer, or any adhesive on the backing or absorbent layer). "Relatively thin" in this context indicates that the layer of hydrogel on one side of the supporting layer is thinner, i.e. has less depth, than the layer of hydrogel on the other side of the supporting layer. The relatively thin layer of hydrogel may be from 10 μm to 500 μm in depth, optionally from 10 μm to 400 μm in depth, optionally from 10 μm to 300 μm in depth, optionally from 10 μm to 200 μm in depth, optionally from 50 μm to 300 μm in depth, optionally from 50 μm to 200 μm in depth, optionally from 50 μm to 100 μm in depth, optionally from 100 μm to 200 μm in depth, optionally from 200 μm to 300 μm in depth.

In an embodiment, a supporting layer, which may be in addition to any supporting layer (e.g. scrim) on or embedded in a side of each island of hydrogel, may be embedded within the interior of each island of hydrogel. For example, in an embodiment a scrim may be present through the central portion of the discrete islands of hydrogel, e.g. in the hydrogel islands at a depth of approximately ⅓ to ⅔ (of the whole depth of the hydrogel island) measured from the side of the hydrogel closest to the wound facing surface to the side of the hydrogel furthest from the wound facing surface.

Optionally, the supporting layer is disposed between at least some, optionally all, of the discrete islands of hydrogel and the backing layer, and in contact with the at least some of the discrete islands of hydrogel. Optionally, an adhesive layer is disposed between, and in contact with, the backing layer and the supporting layer.

Optionally the backing layer comprises a polymeric film, and the supporting layer is a scrim layer, and the scrim layer is a woven or non-woven fabric, or a net, and is optionally formed from non-water absorbent material, which may optionally be or comprise a polyalkene, including, but not limited to polyethylene and polypropylene.

Optionally, the dressing further comprises a layer of absorbent material (which may be termed an absorbent layer herein) disposed on a side of the discontinuous layer of hydrogel facing away from the backing layer; and preferably the absorbent layer does not comprise hydrogel. Optionally, the absorbent layer comprises a water-absorbent open celled foam. Optionally, the absorbent layer comprises a water-absorbent, aromatic or aliphatic polyurethane open celled foam. An aromatic polyurethane is a polyurethane formed from monomers comprising an aromatic group. An aliphatic polyurethane is a polyurethane formed from monomers comprising an aliphatic group. In an embodiment, the absorbent layer extends across the gaps between the discrete islands of hydrogel. In an embodiment, the absorbent layer may extend beyond the area occupied by the discrete islands of hydrogel and contact the backing layer or be adhered to the backing layer, e.g. by an adhesive layer, and in some embodiments, an adhesive on the backing layer may further extend beyond the absorbent layer, so that it can adhere to the skin of a user of the dressing or composition. In an embodiment, the absorbent layer may extend beyond the area occupied by the discrete islands of hydrogel and is adhered to the backing layer in an area completely surrounding the area occupied by the discrete islands of hydrogel; in such an embodiment, the discrete islands of hydrogel may be considered to be enclosed within a parcel formed from the backing layer and the absorbent layer.

Optionally the backing layer comprises an optionally breathable, polymeric film, and the supporting layer is a scrim layer, and the scrim layer is a woven or non-woven fabric, or a net, and is optionally formed from a non-water absorbent material, optionally selected from a polyalkene, including, but not limited to polyethylene and polypropylene, and the dressing further comprises a layer of absorbent material (which may be termed an absorbent layer herein) disposed on a side of the discontinuous layer of hydrogel facing away from the backing layer and the absorbent layer comprises a water-absorbent open celled foam. A breathable polymeric film may be a film that prevents water in liquid form from passing through the film, but allows water vapour to pass through the film.

Optionally, the absorbent layer comprises an antimicrobial agent.

Optionally, the absorbent layer comprises fibres. Optionally, the fibres form a gel when hydrated, which are sometimes termed gel-forming fibres in the art. Optionally, the fibres comprise an alginate, chitosan or a cellulose derivative or any combination thereof. Preferred types of fibre comprise calcium alginate (available from, for example, Foshan United Medical Technologies Ltd, China), and/or sodium polymethacrylate (available, for example, under the tradename Oasis™ from Technical Absorbents Limited). Optionally, the fibres comprise an alginate, optionally calcium alginate, containing in its polysaccharide chain guluronic and/or mannuronic acid, and optionally with a molar ratio of guluronic to mannuronic acid from 90:10 to 10:90, more preferably from 80:20 to 20:80 and even more preferably from 80:20 to 30:70. A particularly preferred fibre comprises an alginate comprising one or more of the following ions, calcium, sodium, zinc and silver. The cellulose derivative may comprise, for example, hydroxypropylmethyl cellulose.

In an embodiment, the composition or dressing further comprises a layer of absorbent material (which may be termed an absorbent layer herein) disposed on a side of the discontinuous layer of hydrogel facing away from the backing layer; and preferably the absorbent layer does not comprise hydrogel, and, preferably, a layer of adhesive is disposed between the layer of absorbent material and at least some of, optionally all of, the discrete islands of hydrogel. The layer of adhesive may be a different material to the hydrogel. In an embodiment, the composition or dressing further comprises a layer of absorbent material (which may be termed an absorbent layer herein) disposed on a side of the discontinuous layer of hydrogel facing away from the backing layer; and preferably the absorbent layer does not comprise hydrogel, and a discontinuous layer, e.g. an apertured layer, of adhesive is disposed between the layer of absorbent material and at least some of, optionally all of, the discrete islands of hydrogel. The discontinuous layer of adhesive may extend across the whole area occupied by the discrete islands of hydrogel, which may or may not include the areas between the islands. The discontinuous layer of adhesive may extend across the whole of the non-wound-facing side of the layer of absorbent material, including any area that extends beyond the area occupied by the islands, such that the discontinuous layer of adhesive can adhere the layer of absorbent material to the backing layer. The adhesive may be any suitable adhesive, which may be or comprise an acrylic adhesive and/or a pressure sensitive adhesive, optionally a pressure sensitive, acrylic adhesive. Optionally, in the embodiments of this paragraph, at least some, optionally all, of the discrete islands of hydrogel have disposed thereon and/or therein a supporting layer.

Optionally, the discrete islands of hydrogel comprise a supporting layer on or embedded in a wound facing side of the islands, wherein the supporting layer, and/or any hydrogel overlying the supporting layer, adheres at least in part to the layer of absorbent material and/or, if present, the discontinuous layer, e.g. an apertured layer, of adhesive on the layer of absorbent material. A further supporting layer may be embedded within the interior of each island of hydrogel. In an embodiment, a further supporting layer may be embedded within the interior of each island of hydrogel. For example, in an embodiment a further scrim may be present through the central portion of the discrete islands of hydrogel, e.g. in the hydrogel islands at a depth of approximately ⅓ to ⅔ (of the whole depth of the hydrogel island) measured from the side of the hydrogel closest to the wound facing surface.

Optionally, the discrete islands of hydrogel comprise a supporting layer on or embedded in a non-wound-facing side of the islands of hydrogel, e.g. a side of the islands that faces away from the absorbent layer, if present, wherein the supporting layer, and/or any hydrogel overlying the supporting layer, may adhere at least in part to the backing layer and/or, if present, a layer of adhesive on the backing layer. In an embodiment, a further supporting layer may be embedded within the interior of each island of hydrogel. For example, in an embodiment a further scrim may be present through the central portion of the discrete islands of hydrogel, e.g. in the hydrogel islands at a depth of approximately ⅓ to ⅔ (of the whole depth of the hydrogel island) measured from the side of the hydrogel closest to the wound facing surface.

The supporting layer on the wound-facing side (or non-wound-facing side) of the discrete islands of hydrogel or on a side of the islands that faces away from the absorbent layer may be as described above, for example the supporting layer may comprise a scrim. The scrim may be a woven or non-woven fabric, or a net, and optionally is non-water absorbent. Preferred scrims include those formed from polyolefins, polyamides, polyacrylates, or polyesters, for example non-wovens, foams or nets. In the embodiments of this paragraph, the discrete islands of hydrogel may directly contact and adhere to the backing layer, such that a separate adhesive is not present between the backing layer and the discrete islands of hydrogel.

Optionally, the supporting layer is present on or in one or more, optionally all, of the discrete islands of hydrogel, and, optionally, no supporting layer is present between the discrete islands. The supporting layer may have been disposed on or in the discrete islands of hydrogel before the combining of the discrete islands of hydrogel with the backing layer and/or the absorbent layer. The supporting layer in or on each island may have been disposed on or in a precursor material to the discrete islands of hydrogel before the precursor material is cured to form the hydrogel.

In an embodiment, the composition or dressing further comprises a layer of absorbent material (which may be termed an absorbent layer herein) disposed on a side of the discontinuous layer of hydrogel facing away from the backing layer and preferably the absorbent layer does not comprise hydrogel; the discrete islands of hydrogel comprise a supporting layer on or embedded in a wound facing side wherein and a discontinuous layer, e.g. an apertured layer, of adhesive is disposed between the layer of absorbent material and at least some of, optionally all of, the discrete islands of hydrogel; and the discontinuous layer of adhesive adheres the layer of absorbent material to the discrete islands of hydrogel, and, optionally, the discrete islands of hydrogel directly contact and adhere to the backing layer, such that a separate adhesive is not present between the backing layer and the discrete islands of hydrogel.

In an embodiment, the composition or dressing further comprises a layer of absorbent material (which may be termed an absorbent layer herein) disposed on a side of the discontinuous layer of hydrogel facing away from the backing layer and preferably the absorbent layer does not comprise hydrogel; the discrete islands of hydrogel comprise a supporting layer on or embedded in a non-wound facing side wherein and a discontinuous layer, e.g. an apertured layer, of adhesive is disposed between the layer of absorbent material and at least some of, optionally all of, the discrete islands of hydrogel; and the discontinuous layer of adhesive adheres the layer of absorbent material to the discrete islands of hydrogel, and optionally the discrete islands of hydrogel and/or any supporting layer thereon or embedded in a non-wound-facing side therein directly contact and adhere to the backing layer, such that a separate adhesive is not present between the backing layer and the discrete islands of hydrogel.

The discontinuous, e.g. apertured, layer of adhesive between the layer of absorbent material and the discrete hydrogel islands may comprise a perforated polymeric film (for example comprising a polymer selected from polyolefin, polyolefin copolymer, polyethylene, ethylene/vinyl acetate copolymer, polyamide and polyurethane) with an adhesive layer on one or both of the wound facing and non wound facing surfaces of the perforated polymeric film. The adhesive on either side of the polymeric film may be of the same composition as or different to one another. Preferably the adhesive of the discontinuous, e.g. apertured, layer of adhesive is an acrylic based pressure sensitive adhesive. The polymeric film is preferably 10-80 µm thick and each of the adhesive layers 1-50 µm thick.

In a preferred embodiment the discontinuous, e.g. apertured, adhesive layer is a pattern coated transfer adhesive. The discontinuous, e.g. apertured, adhesive layer preferably lacks or substantially lacks a hydrogel. Preferably the adhesive is an acrylic based pressure sensitive adhesive with a coat weight of 1-30 $g/m^2$. The apertures in the apertured adhesive layer can be of any shape, for examples circles, ovals, squares, polygons, irregular sided, irregular and maybe arranged in a variety of patterns for example cross hatch or lattice. Preferably the area of each aperture is 1-20 $mm^2$, more preferably 2-16 $mm^2$ and even more preferably 2-9 $mm^2$. The number of apertures present per $cm^2$ of the apertured adhesive layer is preferably from 2-20, more preferably 4-14. In an alternative embodiment, the discontinuous layer of adhesive comprises discrete islands of adhesive, which may each be smaller in area than any of the islands of hydrogel. A plurality of discrete islands of adhesive may extend over each island of hydrogel with which they are in contact. The discrete islands of adhesive may be of any shape, for examples circles, ovals, squares, polygons, irregular sided, irregular and maybe arranged in a variety of patterns. Preferably the area of each discrete island of adhesive is 1-20 $mm^2$, more preferably 2-16 $mm^2$ and even more preferably 2-9 $mm^2$. The number of discrete islands of adhesive present per $cm^2$ of the apertured adhesive layer is preferably from 2-20, more preferably 4-14.

In an embodiment, the discontinuous layer of hydrogel is disposed, in use, on a wound-facing side of the backing layer,
  the composition or dressing further comprises a layer of absorbent material disposed on a side of the discontinuous layer of hydrogel facing away from the backing layer, the layer of absorbent material comprises a water-absorbent open celled foam and/or fibres;
  the discrete islands of hydrogel comprise therein or thereon a supporting layer, (e.g. on or embedded in a wound facing side thereof or a non-wound-facing side thereof), the supporting layer is a scrim layer, and the scrim layer is a woven or non-woven fabric, or a net, and is formed from a non-water absorbent material,
  and a discontinuous layer of adhesive is disposed between the layer of absorbent material and at least some of, optionally all of, the discrete islands of hydrogel;
  and the discontinuous layer of adhesive adheres the layer of absorbent material to the discrete islands of hydrogel, and optionally the discrete islands of hydrogel and/or any supporting layer on or embedded in a backing-layer facing side of the hydrogel, directly contact and adhere to the backing layer. All components of this embodiment may be as defined herein. For examples, in the embodiment of this paragraph, the discontinuous layer of adhesive may be in the form of an apertured layer of adhesive, and optionally the area of each aperture in the apertured layer of adhesive is 2-9 $mm^2$ and/or the number of apertures present per $cm^2$ of the apertured adhesive layer is preferably from 2-20, more preferably 4-14. The discontinuous layer of adhesive may comprise a pressure sensitive adhesive. The discontinuous layer of adhesive may comprise an acrylic adhesive. The discontinuous layer of adhesive may comprise a pressure sensitive, acrylic adhesive In any of the embodiments described above, the absorbent layer and the backing layer may both extend beyond the area occupied by the discrete islands of hydrogel and a layer of adhesive, which may be a discontinuous layer of adhesive as described above, contacts, and adheres the absorbent layer to, the backing layer, preferably around at least part of, optionally all of the perimeter of the area occupied by the discrete islands of hydrogel. In other words, a layer of adhesive, which may be a discontinuous layer of adhesive as described above, occupies at least some of, optionally all of, the area of a surface of the absorbent layer and the backing layer that extends beyond the area occupied by the discrete islands of hydrogel. This effectively encapsulates the discrete islands of hydrogel within the dressing or composition between the absorbent layer and the backing layer.

In any of the embodiments described above, e.g. those having a discontinuous layer of adhesive, the backing layer may be as described herein. For example, the backing layer may comprise a polymeric film. The polymeric film may comprise or be a polyurethane film. Optionally, the polymeric film, which may be or comprise a polyurethane film, is breathable. The polymeric film may have an MVTR of at least 10 $g/m^2/24$ hours, optionally at least at least 50 $g/m^2/24$ hours, optionally at least 100 $g/m^2/24$ hours, optionally at least 200 $gm^2/24$ hours, optionally at least 300 $g/m^2/24$ hours, optionally at least 500 $g/m^2/24$ hours, optionally at least 1000 $g/m^2/24$ hours, with MVTR as measured by the method described in 1993 BP Appendix XX J1. The polymeric film may have an MVTR of from 100 $g/m^2/24$ hours to 10000 g/m²/24 hours, optionally an MVTR of from 100 g/m²/24 hours to 1000 g/m²/24 hours with MVTR as measured by the method described in 1993 BP Appendix XX J1.

The thickness of the backing layer may be less than the thickness of the absorbent layer, if present. The backing layer may have a thickness of from 10 µm to 200 µm, optionally from 10 µm to 150 µm, optionally from 10 µm to 100 µm, optionally from 10 µm to 75 µm, optionally from 10 µm to 50 µm, optionally from 20 µm to 40 µm, optionally about 30 µm.

The absorbent layer, if present, may have a thickness of at least 0.1 mm, optionally at least 0.2 mm, optionally at least 0.3 mm, optionally at least 0.5 mm, optionally at least 1 mm, optionally at least 2 mm, optionally at least 3 mm, optionally at least 4 mm, optionally at least 5 mm. The absorbent layer, if present, may have a thickness of from 0.1 mm to 10 mm, optionally from 0.1 mm to 5 mm, optionally from 0.5 mm to 5 mm, optionally from 1 mm to 5 mm.

The backing layer may have a thickness of from 10 µm to 200 µm, and the absorbent layer may have a thickness of at least 0.3 mm. The backing layer may have a thickness of from 10 µm to 200 µm, and the absorbent layer may have a thickness of from 0.5 mm to 5 mm, optionally from 1 mm to 5 mm, optionally from 2 mm to 4 mm. The backing layer may have a thickness of from 10 µm to 100 µm, and the absorbent layer may have a thickness of from 0.5 mm to 5 mm, optionally from 1 mm to 5 mm, optionally from 2 mm to 4 mm.

Optionally, the backing layer may adhere to the absorbent layer in at least some of, optionally all of, the areas between the discrete islands of hydrogel. Optionally, the the backing layer has raised or embossed portions corresponding to the underlying discrete islands of hydrogel, such that it has a raised or embossed pattern visible on the exterior surface of the backing layer that corresponds to the pattern of the underlying discrete islands of hydrogel, and optionally the backing layer may adhere to the absorbent layer in at least some of, optionally all of, the areas between the discrete islands of hydrogel.

DETAILED DESCRIPTION OF THE INVENTION

Hydrogel

The hydrogel in the dressing or composition preferably consists essentially of a cross-linked hydrophilic polymer of a hydrophilic monomer and optionally one or more comonomer, together with water and/or one or more organic plasticiser, and optionally together with one or more additives selected from surfactants, polymers, pH regulators, electrolytes, chloride sources, bioactive compounds and mixtures thereof, with less than about 10% by weight of other additives. Preferably the hydrogel is made from a precursor solution.

Preferably, the precursor solution is aqueous. The precursor solution may comprise aqueous solutions of one or more monomers that are ionic, non-ionic, amphoteric, zwitterionic or combinations thereof.

The precursor solution preferably contains one or more monomers capable on polymerisation of forming a three-dimensional matrix of cross-linked polymer molecules.

The expressions "polymer", "polymerisation" and like expressions, used herein, includes within its scope homopolymerisation and copolymerisation and the products thereof.

Optionally, the hydrogel comprises a hydrophilic polymer having multiple pendant sulphonyl groups, optionally with multiple pendant carboxylic groups. Optionally, at least some of the pendant sulphonyl groups are in salt form, for example associated with one or more cations, for example selected from sodium and potassium.

Examples of suitable monomers for use in forming the hydrogel, include: 2-acrylamido-2-methylpropane sulphonic acid or a substituted derivative thereof or a salt thereof (e.g. an ammonium or alkali metal salt such as sodium, potassium or lithium salts); acrylic acid or a substituted derivative thereof or a salt thereof (e.g. an alkali metal salt such as sodium, potassium or lithium salt); a polyalkylene glycol acrylate or a substituted derivative thereof; a polyalkylene glycol methacrylate or a substituted derivative thereof; acrylic acid (3-sulphopropyl) ester or a substituted derivative thereof or a salt thereof (e.g. an alkali metal salt such as sodium, potassium or lithium salt); diacetone acrylamide (N-1,1-dimethyl-3-oxobutyl-acrylamide); a vinyl lactam (e.g. N-vinyl pyrrolidone or a substituted derivative thereof); an optionally substituted N-alkylated acrylamide such as hydroxyethyl acrylamide; and an optionally substituted N,N-dialkylated acrylamide; and/or N-acryloyl morpholine or a substituted derivative thereof. Preferably, the polymerisable monomer is selected from the 2-acrylamido-2-methylpropane sulphonic acid, which is optionally in salt form, for example associated with one or more cations, for example selected from sodium and potassium; acrylic acid (3-sulphopropyl) ester, which is optionally in salt form, for example associated with one or more cations, for example selected from sodium and potassium; N-acryloyl morpholine; and hydroxyethyl acrylamide.

The hydrogel used in the present invention preferably comprises a plasticised three-dimensional matrix of cross-linked polymer molecules, and has sufficient structural integrity to be self-supporting even at very high levels of internal water content, with sufficient flexibility to conform to the surface contours of mammalian skin or other surface with which it is in contact.

The hydrogel generally comprises, in addition to the cross-linked polymeric network, an aqueous or non-aqueous plasticising medium including an organic plasticiser. This plasticising medium is preferably present in the same precursor solution as the monomer(s), although if desired it may be applied to the fibrous material separately from the monomer(s) but before polymerisation.

In the material to be polymerised, the precursor solution preferably comprises the monomer(s), cross-linking agent, plasticiser, and optionally water and other ingredients as desired. The polymerisation reaction is preferably a free-radical polymerisation with cross-linking, which may for example be induced by light, heat, radiation (e.g. ionising radiation), or redox catalysts, as is well known.

For example, the free radical polymerisation may be initiated in known manner by light (photoinitiation), particularly ultraviolet light (UV photoinitiation); heat (thermal initiation); electron beam (e-beam initiation); ionising radiation, particularly gamma radiation (gamma initiation); non-ionising radiation, particularly microwave radiation (microwave initiation); or any combination thereof. The precursor solution may include appropriate substances (initiators), at appropriate levels, e.g. up to about 5% by weight, more particularly between about 0.002% and about 2% by weight, which serve to assist the polymerisation and its initiation, in generally known manner.

Preferred photoinitiators include any of the following either alone or in combination:

Type I-α-hydroxy-ketones and benzilidimethyl-ketals e.g. Irgacure 651. These are believed on irradiation to form benzoyl radicals that initiate polymerisation. Photoinitiators of this type that are preferred are those that do not carry substituents in the para position of the aromatic ring. Examples include Irgacure184 and Daracur 1173 as marketed by Ciba Chemicals, as well as combinations thereof.

A particularly preferred photoinitiator is 1-hydroxycyclo-hexyl phenyl ketone; for example, as marketed under the trade name Irgacure 184 by Ciba Speciality Chemicals. Also preferred are (available under the trade name Daracur 1173) and mixtures of 1-hydroxycyclohexyl phenyl ketone and 2-hydroxy-2-propyl phenyl keton, for example mixtures of Irgacure 184 and Daracur 1173.

Photo-polymerisation is particularly suitable, and may be achieved using light, optionally together with other initiators, such as heat and/or ionizing radiation. Photoinitiation will usually be applied by subjecting the pre-gel reaction mixture containing an appropriate photoinitiation agent to ultraviolet (UV) light. The incident UV intensity, at a wavelength in the range from 240 to 420 nm, is typically greater than about 10 mW/cm$^2$. The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers. Those skilled in the art will appreciate that the extent of irradiation will be dependent on a number of factors, including the UV intensity, the type of UV source used, the photoinitiator quantum yield, the amount of monomer(s) present, the nature of the monomer(s) present and the presence of polymerisation inhibitor.

After completion of the polymerisation, the hydrogel is preferably sterilised in conventional manner.

If desired, certain ingredients of the hydrogel may be added after the polymerisation and optional cross-linking reaction. However, it is generally preferred that substantially all of the final ingredients of the hydrogel are present in the precursor solution, and that—apart from minor conventional conditioning or, in some cases, subsequent modifications caused by the sterilisation procedure—substantially no chemical modification of the hydrogel takes place after completion of the polymerisation reaction.

Monomers

Optional substituents of the monomers used to prepare the hydrogels used in the present invention may preferably to selected from substituents which are known in the art or are reasonably expected to provide polymerisable monomers which form hydrogel polymers having the properties necessary for the present invention. Suitable substituents include, for example, lower alkyl, hydroxy, halo and amino groups.

Particularly preferred monomers include: the sodium salt of 2-acrylamido-2-methylpropane sulphonic acid, commonly known as NaAMPS, which is available commercially at present from Lubrizol as either a 50% aqueous solution (reference code LZ2405) or a 58% aqueous solution (reference code LZ2405A); acrylic acid (3-sulphopropyl) ester potassium salt, commonly known as SPA or SPAK (SPA or SPAK is available commercially in the form of a pure solid from Raschig); N-acryloyl morpholine; and hydroxyethyl acrylamide.

Cross-Linking Agents

Conventional cross-linking agents can be used to provide the necessary mechanical stability and to control the adhesive properties of the hydrogel. The amount of cross-linking agent required will be readily apparent to those skilled in the art such as from about 0.01% to about 0.5%, particularly from about 0.05% to about 0.4%, most particularly from about 0.08% to about 0.3%, by weight of the total polymerisation reaction mixture. Typical cross-linkers include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide.

Organic Plasticisers

One or more organic plasticisers may be present in the hydrogel and/or the hydrogel precursor solution. The one or more organic plasticisers, when present, may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticiser. An alternative preferred plasticiser is the ester derived from boric acid and glycerol. When present, the organic plasticiser may comprise up to about 45% by weight of the hydrogel composition.

Surfactants

Any compatible surfactant may optionally be used as an additional ingredient of the hydrogel composition. Surfactants can lower the surface tension of the mixture before polymerisation and thus aid processing. The surfactant or surfactants may be non-ionic, anionic, zwitterionic or cationic, alone or in any mixture or combination. The surfactant may itself be reactive, i.e. capable of participating in the hydrogel-forming reaction. The total amount of surfactant, if present, is suitably up to about 10% by weight of the hydrogel composition, preferably from about 0.05% to about 4% by weight.

In a preferred embodiment of the invention the surfactant comprises at least one propylene oxide/ethylene oxide block copolymer, for example such as that supplied by BASF Plc under the trade name Pluronic P65 or L64.

Other Additives

The hydrogel may include one or more additional ingredients, which may be added to the pre-polymerisation mixture or the polymerised product, at the choice of the skilled worker. Such additional ingredients may be selected from additives, including, for example, water, organic plasticisers, surfactants, polymeric material (hydrophobic or hydrophilic in nature, including proteins, enzymes, naturally occurring polymers and gums), synthetic polymers with and without pendant carboxylic acids, electrolytes, pH regulators, colorants, chloride sources, bioactive compounds and mixtures thereof. The polymers can be natural polymers (e.g. xanthan gum), synthetic polymers (e.g. polyoxypropylene-polyoxyethylene block copolymer or poly-(methyl vinyl ether alt maleic anhydride)), or any combination thereof. "Bioactive compounds" may indicate any compound or mixture included within the hydrogel for some effect it has on living systems, whether the living system be bacteria or other microorganisms or higher animals such as the patient. Bioactive compounds that may be mentioned include, for example, pharmaceutically active compounds, antimicrobial agents, antiseptic agents, antibiotics and any combination thereof. Antimicrobial agents may, for example, include: sources of oxygen and/or iodine (e.g. hydrogen peroxide or a source thereof and/or an iodide salt such as potassium iodide) (see, for example Bioxzyme™ technology, for example in The Sunday Telegraph (UK) 26 Jan. 2003 or the discussion of the Oxyzyme™ system at www.wounds-uk-.com/posterabstracts2003.pdf); honey (e.g. active Manuka honey); antimicrobial metals, metal ions and salts, such as, for example, silver-containg antimicrobial agents (e.g. colloidal silver, silver oxide, silver nitrate, silver thiosulphate, silver sulphadiazine, or any combination thereof); or any combination thereof.

Hydrogels incorporating antimicrobial agents may, for example, be active against such organisms as *Staphylococcus aureus* and *Pseudomonas aeruginosa*.

Agents for stimulating the healing of wounds and/or for restricting or preventing scarring may be incorporated into the hydrogel. Examples of such agents include growth factors e.g. from GroPep Ltd, Australia or Procyte, USA (see, e.g. WO-A-96/02270, the contents of which are incorporated herein by reference); cell nutrients (see, e.g., WO-A-93/04691, the contents of which are incorporated herein by reference); glucose (see, e.g., WO-A-93/10795, the contents of which are incorporated herein by reference); an anabolic hormone or hormone mixture such as insulin, triiodothyronine, thyroxine or any combination thereof (see, e.g., WO-A-93/04691, the contents of which are incorporated herein by reference); or any combination thereof.

Additional polymer(s), typically rheology modifying polymer(s), may be incorporated into the polymerisation reaction mixture at levels typically up to about 10% by weight of total polymerisation reaction mixture, e.g. from about 0.2% to about 10% by weight. Such polymer(s) may include polyacrylamide, poly-NaAMPS, polyethylene glycol (PEG), polyvinylpyrrolidone (PVP) or carboxymethyl cellulose.

The hydrogel in the composite of the present invention preferably consists essentially of a cross-linked hydrophilic polymer of a hydrophilic monomer and optionally one or more comonomer, together with water and/or one or more organic plasticiser, and optionally together with one or more additives selected from surfactants, polymers, pH regulators, electrolytes, chloride sources, bioactive compounds and mixtures thereof, with less than about 10% by weight of other additives.

The hydrogel may be formed by disposing a layer of precursor solution on a substrate, then curing the precursor solution to form the hydrogel, and cutting portions of the hydrogel and disposing them on a backing layer, to form the discrete islands of the hydrogel. In an alternative embodiment, the discrete islands of hydrogel may be formed in-situ, from a precursor solution on the backing layer.

For further details of the hydrogel material for use in the present invention, and its preparation, please refer to the following publications: PCT Patent Applications Nos. WO-97/24149, WO-97/34947, WO-00/06214, WO-00/06215, WO-00/07638, WO-00/46319, WO-00/65143 and WO-01/96422, the disclosures of which are incorporated herein by reference.

Hydrogel with Supporting Layer

Each of the discrete hydrogel islands may suitably be present as a thin sheet, preferably supported by a sheet support member to provide mechanical strength; the sheet support member may be termed a supporting layer herein. The sheet support member for the hydrogel may, for example, be or comprise a scrim or net structure, for example formed of a synthetic and/or natural polymer such as polyethylene or polypropylene or polyester. The sheet support member for the hydrogel may overlie at least some, optionally all, the discrete islands of hydrogel on a face of the islands directed away from a wound in use, i.e. on a face of the islands disposed toward the backing layer, or may be embedded within the hydrogel polymer.

The backing layer and/or (if present) the sheet support member may, if desired, extend beyond the margins of the area occupied by the discrete islands of hydrogel, and may be provided with a skin adhesive portion to secure the dressing to the skin. In an embodiment, the discrete islands of hydrogel occupy an approximately central portion of the backing layer, and the backing layer extends beyond the central portion and is provided adhesive around the central portion, such that an adhesive seal can be formed when the dressing is placed on a skin of a user. The skin adhesive portion may be hydrogel in nature (for example a plasticised tacky hydrogel, which may be the same as or different from the hydrogel provided on the support member for the treatment according to the present invention), or may be another type of skin adhesive selected from the many skin adhesives known in the wound dressings art.

The precursor solution may be dispensed onto a substrate in a continuous or non-continuous manner and the supporting layer structure placed on top, using the absorbancy characteristics of the support layer to take up at least in part the precursor solution.

The support structure in contact with the precursor solution may suitably be in the form of a layer. This layer may suitably be provided for the polymerisation on a surface, most preferably itself provided with a release layer such as siliconised paper of plastic. After polymerisation of such an arrangement, the resultant hydrogel/support layer composite will be in the form of a sheet having its underside protected by a release layer.

Backing Layer

The backing layer may for example comprise a polymeric film. It may be of a composite multilayered structure for example a film/foam laminate. The polymeric film preferably has a moisture transmission rate greater than 30 $g/m^2/24\ hr$, more preferably greater than 300 $g/m^2/24\ hr$ and even more preferably greater than 600 $g/m^2/24\ hr$. Preferably the polymeric film is a breathable and/or hydrophilic polyurethane. The backing layer, for example before and at the time of adhering to the discrete islands of hydrogel, may be substantially continuous, i.e. having no through-apertures, and/or may be flat, i.e. substantially lacking or lacking any depressions or indentations or raised portions. For example, the backing layer has no depressions or indentations or raised portions produced in a manner such as thermoforming, which would produce a sheet having substantially permanent depressions or indentations or raised portions.

An adhesive, for example an acrylic adhesive, may be coated onto the backing layer. The adhesive may fully coat or only partially coat the backing layer. When present only as a partial coating it is preferred that the adhesive forms a regular pattern.

In an embodiment, the backing layer directly contacts and adheres to the discrete islands of hydrogel.

Formation of Discrete Islands of Hydrogel

The discrete islands of hydrogel may be formed by first forming a sheet of hydrogel and then cutting and removing a desired size and shape of islands from the sheet, and then placing them on a backing layer. Preferably the islands are cut using a shaped die. The hydrogel shapes are then assembled into an array of desired shaped and separation between the islands on a backing layer. When the hydrogel islands have a supporting layer and the backing layer is coated at least in part with adhesive then the discrete hydrogel islands, when disposed with the support layer facing the adhesive, will be held in place. Preferably the total area occupied by the array of discrete hydrogel islands disposed on the backing sheet is less than the area of the backing sheet. This allows the backing sheet to form a border region around the array of discrete hydrogel slands. When an adhesive is present on the backing layer and is orientated to facing the skin, the overlap of the backing layer can provide and adhesive means directly or indirectly to the skin.

Additional Absorbent Layer

An additional absorbent layer may be disposed on the wound facing side of the discrete islands of hydrogel. The absorbent layer may comprise a foam, preferably an open cell foam, preferably a hydrophilc aromatic or aliphatic polyurethane foam. The absorbent layer may comprise a fibre, preferably a fibre that swells in saline solution. Preferably the fibre is in the form of a non woven material and preferably the fibres comprise an alginate, chitosan or a cellulose derivative or any combination thereof. The additional absorbent layer may also comprise a multilayer structure. The additional absorbent layer may also have a keying layer on the non wound facing side to attach it to the wound facing side of the discrete hydrogel islands. A keying layer may act to adhere two layers together, preferably by merging into one or both of the two adjacent layers it is adhering together.

When the backing layer is at least in part coated with adhesive and the backing layer extends beyond the perimeter of the array of discrete hydrogel islands then the adhesive on the backing layer may adhere the additional absorbent layer to the backing layer and encapsulate the array of discrete hydrogel islands.

Figure 1:
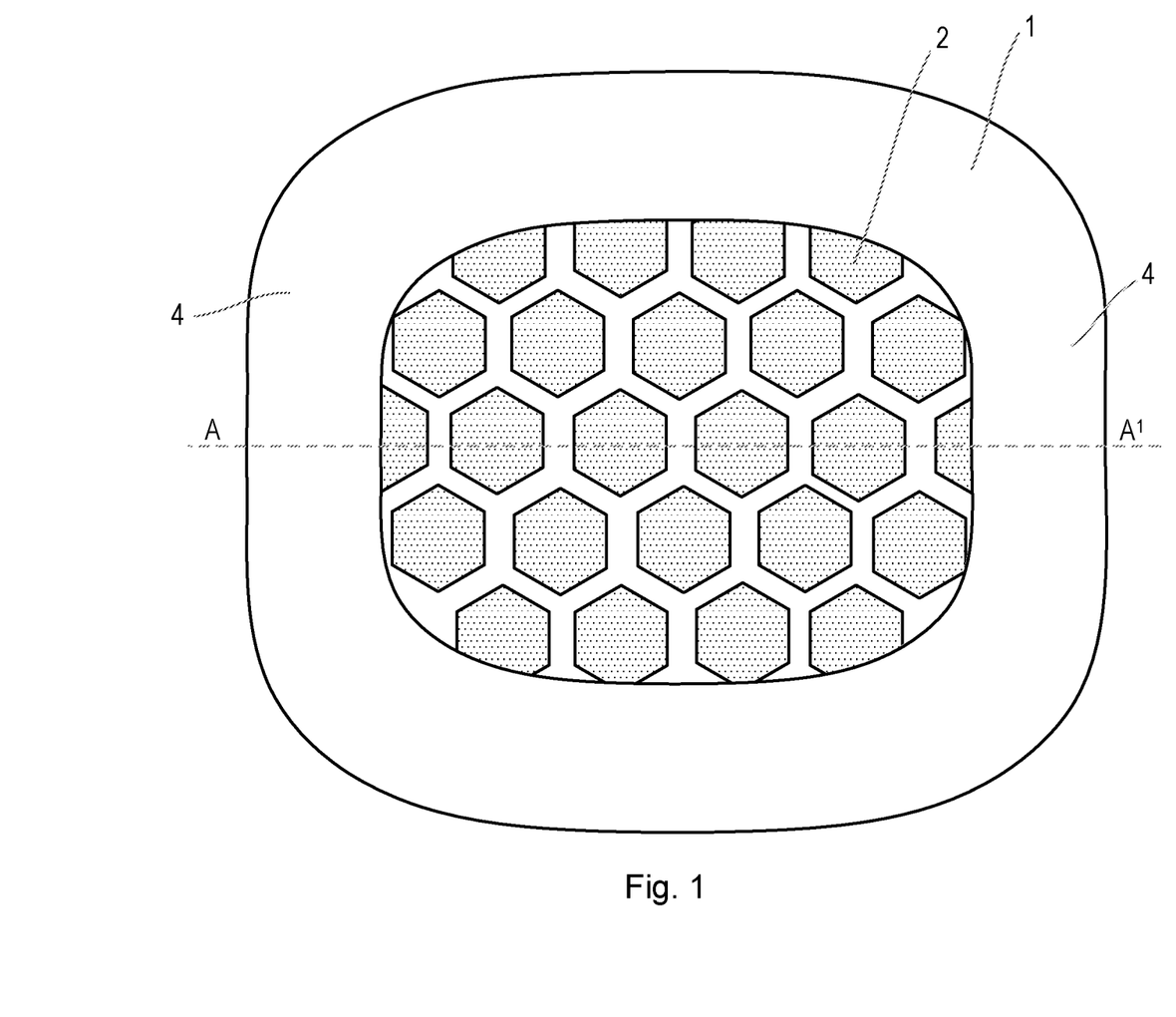
FIG. 1 shows an embodiment of the dressing or composition described herein, when viewed from an angle perpendicular to the plane of the backing layer.
Figure 2:
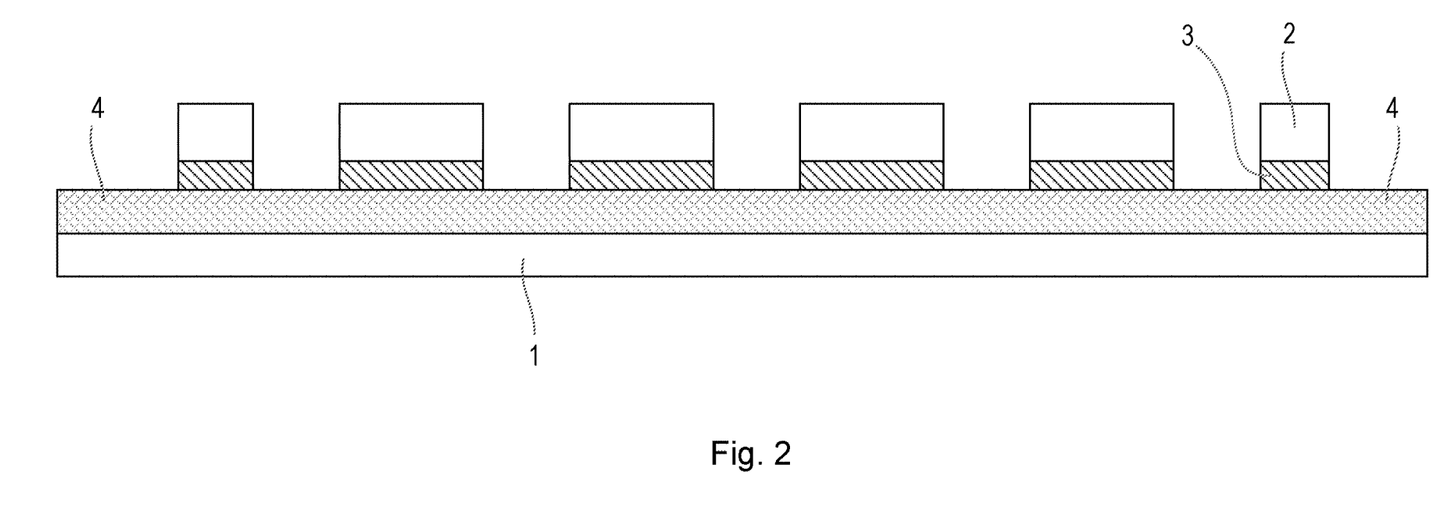
FIG. 2 shows a cross-sectional view of the embodiment of the dressing or composition shown in FIG. 1.
Figure 3:
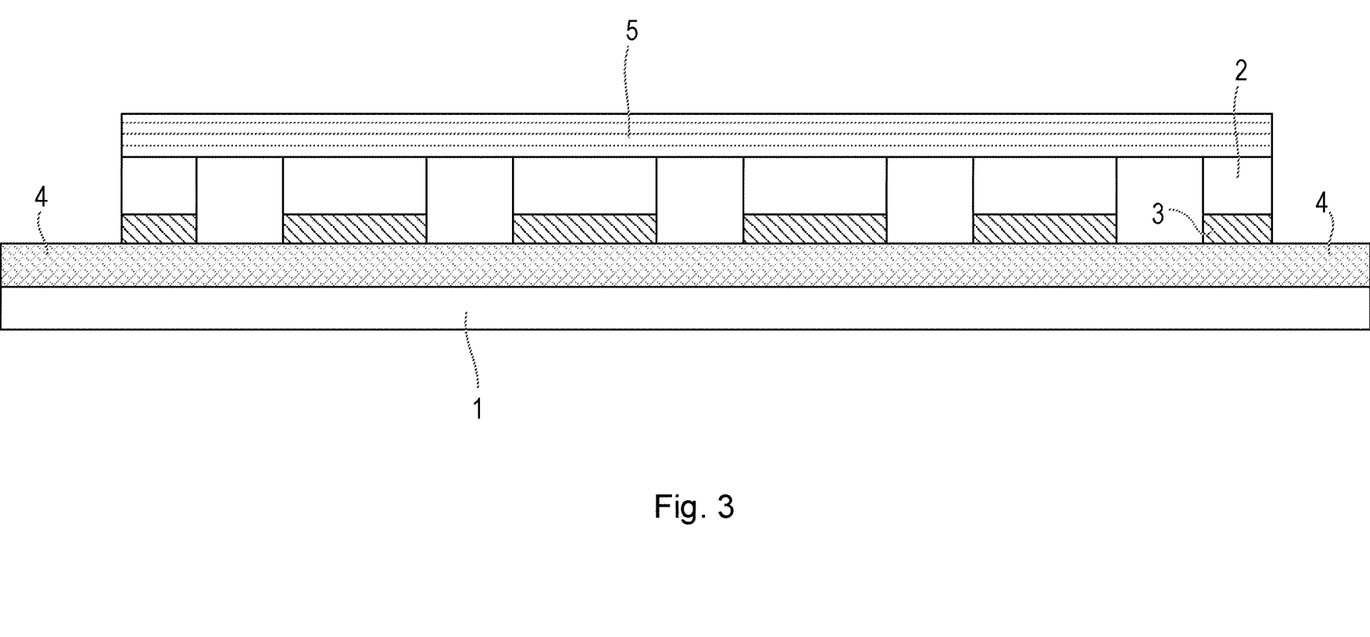
FIG. 3 shows a cross-sectional view of a further embodiment of the dressing or composition described herein, the dressing or composition further comprising an absorbent layer disposed on the discrete islands of hydrogel.

FIGS. 1, 2 and 3 illustrate schematically embodiments of the dressing or composition as described herein. FIG. 1 shows an embodiment of the dressing or composition described herein, when viewed from an angle perpendicular to the plane of the backing layer. In this Figure, a backing layer 1, is shown, having disposed thereon discrete islands 2 of hydrogel. The backing layer may, for example, be a breathable polymeric film, e.g. a breathable polyurethane film. An adhesive 4 is present on the area surrounding the area occupied by the discrete islands of hydrogel. The adhesive may be a pressure-sensitive acrylic adhesive. A line A-A$^1$ is marked on FIG. 1, for the purpose of illustrating the cross section taken for FIG. 2.

FIG. 2 shows a cross-sectional view along the line A-A$^1$ of the embodiment of the dressing or composition shown in FIG. 1. The discrete islands of hydrogel 2 can be seen to be disposed on the backing layer 1, and a supporting layer 3 is disposed between each island of hydrogel and the backing layer. The supporting layer 3 may, for example, by a scrim, for example a polypropylene scrim. The supporting layer 3 is adhered to the backing layer by means of an adhesive 4. As seen in FIG. 1, adhesive 4 extends beyond the area occupied by the discrete islands of hydrogel, to allow the adhesive to adhere the dressing or composition to the skin of a user of the dressing.

FIG. 3 shows a schematic cross-sectional view of a further embodiment of the dressing or composition, the dressing or composition is similar to that of FIG. 2, except that it further comprises an absorbent layer 5 disposed on the discrete islands of hydrogel. The absorbent layer 5 extends across the gaps between the discrete islands of hydrogel. In some embodiments, the absorbent layer 5 may extend beyond the area occupied by the discrete islands of hydrogel and extend downward so that it contacts the adhesive layer 4, and in some embodiments, the adhesive may further extend beyond the absorbent layer 5, so that it can adhere to the skin of a user of the dressing or composition. The absorbent layer 5 may comprise a water-absorbent open-celled foam.

Figure 4:
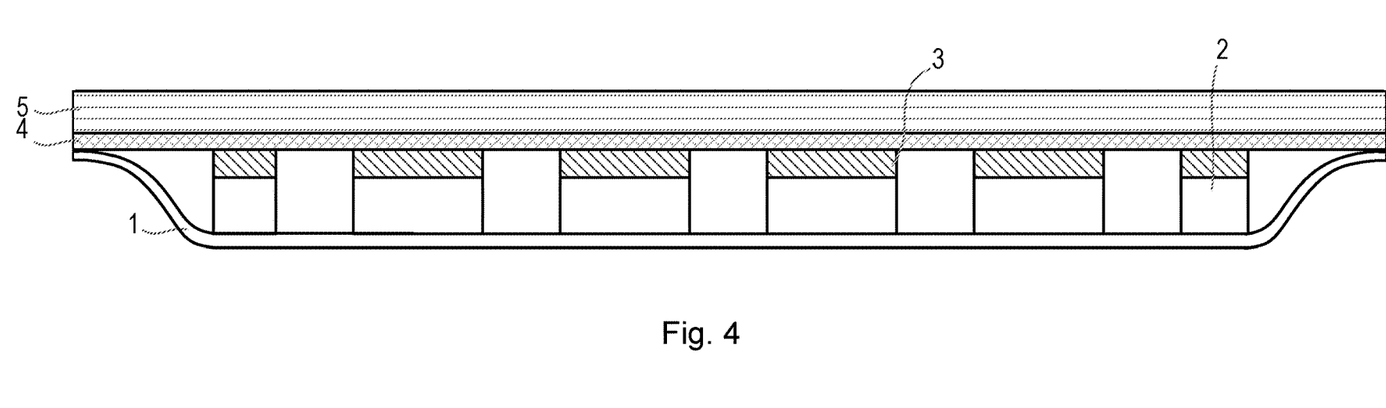
FIG. 4 shows a cross-sectional view of a further embodiment of the dressing or composition described herein, the dressing or composition further comprising an absorbent layer 5, and a discontinuous layer of adhesive 4 is disposed on a side of the absorbent layer 5 facing toward the discrete islands of hydrogel 2. The discrete islands of hydrogel 2 can be seen to be disposed on, and in direct contact with, the backing layer 1, with a supporting layer 3, which may be in the form of a scrim, embedded in a side of the hydrogel disposed closest to the absorbent layer 5. The discrete islands of hydrogel 2 are encapsulated between the absorbent layer 5 and the backing layer 1, which are adhered together around the perimeter of the area occupied by the discrete islands of hydrogel 2.

FIG. 4 shows a schematic cross-sectional view of a further embodiment of the dressing or composition. In this embodiment, the discrete islands of hydrogel 2 can be seen to be disposed on, and in direct contact with, the backing layer 1, and a supporting layer 3 is embedded in each island of hydrogel on a side disposed closest to the absorbent layer 5 (i.e. a side of the hydrogel facing away from the backing layer). As a result of the embedding of the supporting layer in the hydrogel, a thin layer of hydrogel, e.g. from about 10 μm to 300 μm, may be present between the supporting layer and the adhesive 4 on the absorbent layer 5. A further supporting layer (not shown) may be embedded within the interior of each island of hydrogel. For example, in an embodiment a further scrim (not shown) may be present through the central portion of the discrete islands of hydrogel, e.g. in the hydrogel islands at a depth of approximately ⅓ to ⅔ measured from the side of the hydrogel closest to the wound facing surface. The absorbent layer 5 may comprise a water-absorbent open-celled foam. A discontinuous layer of adhesive 4 covers the side of the absorbent layer 5 facing away from the wound, i.e. facing toward the discrete islands of hydrogel (for simplicity discontinuities in the adhesive layer are not shown in figure). The discontinuous layer of adhesive 4 may be in the form of an apertured layer of adhesive. The absorbent layer 5 and the backing layer 1 may extend beyond the area occupied by the discrete islands of hydrogel so that discontinuous layer of adhesive 4 can contact, and adhere the absorbent layer 5 to, the backing layer 1. In an embodiment (not shown), the backing layer 1 is thinner than the absorbent layer 5 and the backing layer 1 has raised or embossed portions corresponding to the underlying discrete islands of hydrogel, such that it has a raised or embossed pattern visible on the exterior surface of the backing layer that corresponds to the pattern of the underlying discrete islands of hydrogel, and the backing layer adheres to the absorbent layer in at least some of, optionally all of, the areas between the discrete islands of hydrogel.

Figure 5:
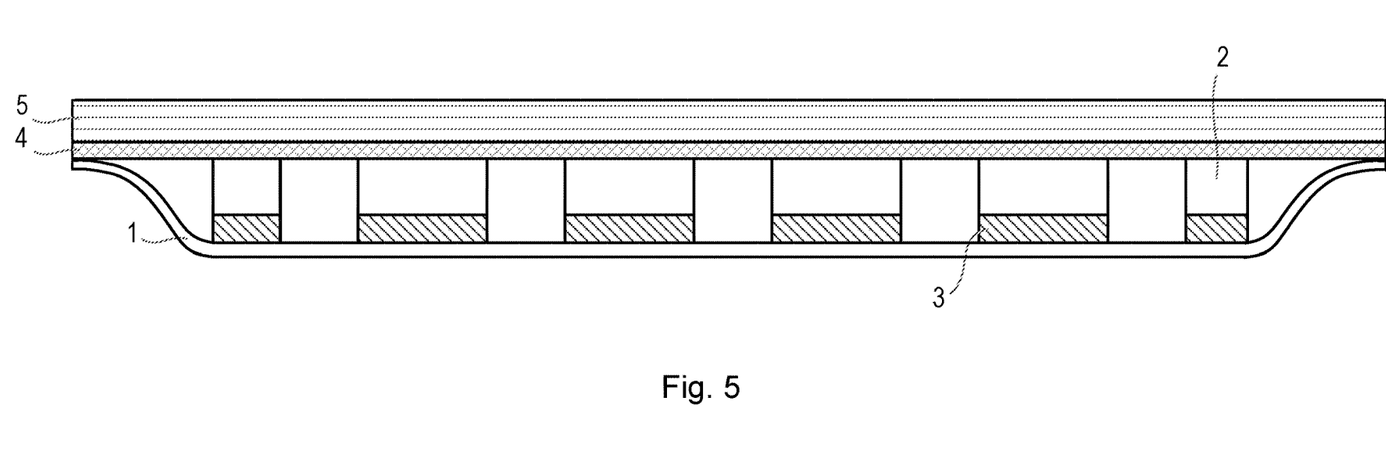
FIG. 5 shows a cross-sectional view of a further embodiment of the dressing or composition described herein, the dressing or composition further comprising an absorbent layer 5, and a discontinuous layer of adhesive 4 is disposed on a side of the absorbent layer 5 facing toward the discrete islands of hydrogel. The discrete islands of hydrogel 2 are disposed on, and in direct contact with, the backing layer 1, with a supporting layer 3, which may be in the form of a scrim, embedded in a side of the hydrogel disposed closest to the backing layer 1.

FIG. 5 shows a schematic cross-sectional view of a further embodiment of the dressing or composition described herein that is the same as the embodiment shown in FIG. 4, with the exception that the supporting layer 3, which may be in the form of a scrim, is embedded in a side of the hydrogel disposed closest to the backing layer 1 (i.e. a side of the hydrogel facing away from the absorbent layer). As a result of the embedding of the supporting layer in the hydrogel, a thin layer of hydrogel, e.g. from about 10 µm to 300 µm, may be present between the supporting layer 3 and the backing layer 1. This arrangement of the layers was found to have improved breathability compared to the dressing of FIG. 3, while still having similar fluid handling capabilities, e.g. in terms of quantity and rate of fluid absorption, and still being very flexible. In an embodiment (not shown), the backing layer 1 is thinner than the absorbent layer 5 and the backing layer 1 has raised or embossed portions corresponding to the underlying discrete islands of hydrogel, such that it has a raised or embossed pattern visible on the exterior surface of the backing layer that corresponds to the pattern of the underlying discrete islands of hydrogel, and the backing layer adheres to the absorbent layer in at least some of, optionally all of, the areas between the discrete islands of hydrogel.

The present invention will now be further described with reference to the following non-limiting Examples.

EXAMPLES

In these examples, the pre-gel formulations was cured as 0.3 to 2.6 kg per square metre coat weight by a medium pressure mercury arc lamp (GEW, UK).

Example 1

Pre-gel: 70 parts by weight of 58% aqueous solution of the sodium salt of acrylamidomethylpropanesulphonic acid (Na AMPS, LZ2405 Lubrizol), 30 parts glycerol and 0.14 parts of a 1 to 10 (by weight) mixture of Daracure 1173 photoinitiator (BASF) and IRR280 cross-linker (PEG400 diacrylate, UCB Chemicals).

Example 2

The pre-gel from example 1 was dispensed onto a siliconised polyester to a coat weight of 1 kg/m². A 20 gsm non woven polypropylene scrim (RKW) was then placed on top of the pre-gel and then cured with a medium pressure mercury arc lamp (GEW, UK) to form a sheet of hydrogel with a support layer. The support layer, i.e. the scrim, can be described as being within the surface region of the hydrogel.

Example 3

10 mm diameter circles were cut from the sheet produced in Example 2 and placed on a square piece of fully adhesive coated polyurethane film (Inspire 2331, Exopak UK)(100 mm by 100 mm) in a rectangular array (20 islands in a 5 by 4 configuration with a 3 mm separation between each island). The perimeter of the rectangular array was 62 mm long by 49 mm wide.

Example 4

10 mm diameter circles were cut from the sheet produced in Example 2 and placed on a square piece of fully adhesive coated polyurethane film (Inspire 2331, Exopak UK)(100 mm by 100 mm) in a rectangular array (20 islands in a 5 by 4 configuration with a 3 mm separation between each island). The adhesive was an acrylic, pressure sensitive adhesive. The perimeter of the rectangular array was 62 mm long by 49 mm wide. A 100 mm by 100 mm hydrophilic foam (Copura) was then placed onto the adhesive/discrete hydrogel island array to form a wound dressing with a wound facing additional absorbent foam layer. The assembled dressing had excellent flexibility. The assembled dressing had fluid handling capabilities, e.g. in terms of quantity and rate of fluid absorption, comparable to the dressing of Example 5.

Example 5 (Comparative)

A 62 mm by 49 mm continuous sample was cut from the sheet produced in Example 2 and placed on a square piece of fully adhesive coated polyurethane film (Inspire 2331, Exopak UK)(100 mm by 100 mm) A 100 mm by 100 mm hydrophilic foam (Copura) was then placed onto the hydrogel sheet to form a wound dressing with a wound facing additional absorbent foam layer. The assembled dressing had a reduced flexibility when compared to Example 4.

Example 6

10 mm diameter circles were cut from the sheet produced in Example 2 and placed on a square piece of patterned adhesive coated polyurethane film (Dev13.12A, Exopak UK)(100 mm by 100 mm) in a rectangular array (20 islands in a 5 by 4 configuration with a 3 mm separation between each island). The perimeter of the rectangular array was 62 mm long by 49 mm wide. A 100 mm by 100 mm hydrophilic foam (Copura) was then placed onto the adhesive/discrete hydrogel island array to form a wound dressing with a wound facing additional absorbent foam layer. The assembled dressing had fluid handling capabilities, e.g. in terms of quantity and rate of fluid absorption, comparable to the dressing of Example 5. It was found that this dressing had improved breathability compared to the dressing of Example 4.

Example 7

Pre-gel: 57 parts by weight of 58% aqueous solution of the sodium salt of acrylamidomethylpropanesulphonic acid (Na AMPS, LZ2405 Lubrizol), 10 parts acrylic acid (3-sulphopropyl) ester potassium salt, (Raschig), 30 parts glycerol, 2 parts acrylic acid (BASF) and 0.1 parts of a 1 to 10 (by weight) mixture of Daracure 1173 photoinitiator (BASF) and IRR280 cross-linker (PEG400 diacrylate, UCB Chemicals).

Example 8

The pre-gel from example 7 was dispensed onto a siliconised polyester to a coat weight of 0.7 kg/m². A 25 g/m² non woven polyethylene/polyester scrim (HDK, 5722)) was then placed on top of the pre-gel and then cured with a medium pressure mercury arc lamp (GEW, UK) to form a sheet of hydrogel with a support layer in the surface of the hydrogel. A further 0.3 kg/m² of the pre-gel formulation from example 7 was dispensed onto the non woven scrim surface of the just made sheet hydrogel and a polypropylene based 20 g/m² (RKW, 040020001) non woven scrim was then placed on top of the pre-gel and then cured with a medium pressure mercury arc lamp (GEW, UK) to form a sheet of hydrogel with a support layer within the bulk of the hydrogel matrix and another support layer within in the surface region of the final hydrogel sheet assembly.

Example 9

10 mm diameter circles were cut from the sheet matrix produced in Example 8. The surfaces of the hydrogel circles comprising the polyester non woven scrim were placed on a square piece of polyurethane film (Coveris 2352 with the polyethylene terephthalate carrier removed) 100 mm by 100 mm) in a rectangular array (20 islands in a 5 by 4 configuration with a 3 mm separation between each island). The perimeter of the rectangular array was 62 mm long by 49 mm wide. A 100 mm by 100 mm hydrophilic foam (Copura) with a pattern coated transfer adhesive (PCTA) (Scapa Tapes, US, Bioflex Rx1240U, carriers removed) laminated to the non wound facing surface of the foam was then placed onto the polyurethane film/discrete hydrogel island array. The assembled components were then compressed to adhere the outer polyurethane film to the discrete hydrogel islands and the PCTA layer around the perimeter of the rectangular array of discrete hydrogel islands and in addition between each of the discrete islands to form a wound dressing with a wound facing additional absorbent foam layer. The assembled dressing had fluid handling capabilities, e.g. in terms of quantity and rate of fluid absorption, comparable to the dressing of Example 5. It was found that this dressing had improved breathability compared to the dressing of Example 4.

The invention claimed is:

1. A wound dressing having improved flexibility for application to the various contours of the body, comprising a backing layer having disposed thereon a discontinuous layer of hydrogel, wherein the discontinuous layer of hydrogel is in the form of discrete islands of hydrogel on the backing layer that are not linked by hydrogel,
wherein, in use, an adhesive layer is disposed on at least a part of a wound-facing side of the backing layer, and the adhesive can act to adhere the discrete islands of hydrogel, and, if present any supporting layer on the discrete islands, to the backing layer and/or can adhere the wound dressing to the skin of a user of the dressing.

2. The wound dressing according to claim 1, wherein the islands, when viewed from an angle perpendicular to the backing layer, each have shape selected from a regular shape and an irregular shape.

3. The wound dressing according to claim 2, wherein the islands each have a shape selected from polygons, dots and crosses.

4. The wound dressing according to claim 1, wherein the closest distance between two adjacent islands of hydrogel is from 50 to 5000 microns.

5. The wound dressing according to claim 1, wherein at least some of the discrete islands each have an area, extending across the backing layer, of from 5 to 500 mm².

6. The wound dressing according to claim 1, wherein the discontinuous layer of hydrogel is disposed on a wound-facing side of the backing layer.

7. The wound dressing according to claim 1, wherein the backing layer comprises a polymeric film.

8. The wound dressing according to claim 7, wherein the polymeric film is a polyurethane film.

9. The wound dressing according to claim 8, wherein the polyurethane film is breathable.

10. The wound dressing according to claim 1, wherein, an adhesive is disposed between the backing layer and at least some of the discrete islands of hydrogel.

11. The wound dressing according to claim 1, wherein the discrete islands of hydrogel comprise a supporting layer on a non-wound facing side wherein the supporting layer adheres at least in part to the backing layer and or adhesive layer.

12. The wound dressing according to claim 11, wherein the backing layer comprises a polymeric film, and the supporting layer is a scrim layer.

13. The wound dressing according to claim 12, wherein the scrim layer is a woven or non-woven fabric, or a net.

14. The wound dressing according to claim 1, wherein at least some of the discrete islands of hydrogel have disposed thereon or therein a supporting layer.

15. The wound dressing according to claim 14, wherein the supporting layer is disposed between the at least some of the discrete islands of hydrogel and the backing layer, and in contact with the at least some of the discrete islands of hydrogel.

16. The wound dressing according to claim 15, wherein an adhesive layer is disposed between, and in contact with, the backing layer and the supporting layer.

17. A method of treating a wound, the method comprising applying a wound dressing according to claim 1 to the wound, and wherein the hydrogel is disposed between the backing layer and the wound.

18. A method of forming a wound dressing according to claim 1, the method comprising: forming discrete shaped islands of hydrogel and arranging them into an array disposed on a backing layer.

* * * * *